US010000527B2

(12) United States Patent
Sudhir et al.

(10) Patent No.: US 10,000,527 B2
(45) Date of Patent: Jun. 19, 2018

(54) 11-SUBSTITUTED BILE ACID DERIVATIVES, PROCESS FOR THE PREPARATION THEREOF AND USE OF THESE COMPOUNDS AS MEDICAMENTS

(71) Applicant: Council of Scientific and Industrial Research, New Delhi (IN)

(72) Inventors: Pore Vandana Sudhir, Pune (IN); Jaisingh Manohar Divse, Pune (IN); Chaitanya Rajendra Charolkar, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days. days.

(21) Appl. No.: 15/103,291

(22) PCT Filed: Nov. 24, 2014

(86) PCT No.: PCT/IN2014/000730
§ 371 (c)(1),
(2) Date: Jun. 9, 2016

(87) PCT Pub. No.: WO2015/087340
PCT Pub. Date: Jun. 18, 2015

(65) Prior Publication Data
US 2016/0311848 A1    Oct. 27, 2016

(30) Foreign Application Priority Data
Dec. 12, 2013  (IN) .......................... 3619/DEL/2013

(51) Int. Cl.
*A61K 31/575* (2006.01)
*A61K 31/58* (2006.01)
*C07J 41/00* (2006.01)
*C07J 43/00* (2006.01)

(52) U.S. Cl.
CPC ......... *C07J 41/0005* (2013.01); *C07J 43/003* (2013.01)

(58) Field of Classification Search
CPC ....... C07J 41/0005; C07J 43/003; C07J 75/00
USPC .......... 514/176, 179; 540/106, 107; 552/515
See application file for complete search history.

(56) References Cited

U.S. PATENT DOCUMENTS 2,485,253 A    10/1949   Berezeller

FOREIGN PATENT DOCUMENTS

| FR | 1271490 | 9/1961 |
| WO | WO-02/14342 A1 | 2/2002 |
| WO | WO-2010/014836 | 2/2010 |
| WO | WO-2015/087340 | 6/2015 |

OTHER PUBLICATIONS

Aher Nilkanth G., et al., "Synthesis of Bile Acid Dimers Linked with 1,2,3-Triazole Ring at C-3, C-11, and C-24 Positions", *Synlett*, No. 14, (2005), 2155-2158.
Breslow, Ronald, et al., "Biomimtic Control of Chemical Selectivity", *Acc. Chem. Res.*, 13, (1980), 170-177.
Harburn, James J., et al., "Synthesis of Novel Steroidal Inhibitors of HIV-I Protease", *Tetrahedron*, 54(39), (1998), 11907-11924.
Peterson, D. H., et al., "Microbiological Transformations of Steroids. I. Introduction of Oxygen at Carbon-11 of Progeserone", *J. Am. Chem. Soc.*, 74, (1952), 5933-5936.
Salunke, Deepak B., et al., "Amino Functionalized Novel Cholic Acid Derivatives Induce HIV-1 Replication and Syncytia Formation in T Cells", *J. Med. Chem.*, 49(8), (2006), 2652-2655.
Salunke, Deepak B., et al., "An efficient method for the synthesis of methyl 11α-amino-3α,7α-diacetoxy-12-oxo-5β-cholan-24-oate", *Tetrahedron*, 61(14), (Apr. 2005), 3605-3612.
"International Application No. PCT/IN2014/000730, International Search Report and Written Opinion dated Mar. 13, 2015", (Mar. 13, 2015), 8 pgs.
Epstein, D., et al., "The effect of physiological concentrations of bile acids on the in vitro growth of *Mycobacterium tuberculosis*", South African Medical Journal, vol. 102, No. 6 (2012), (2012), 522-524.

*Primary Examiner* — Barbara P Badio
(74) *Attorney, Agent, or Firm* — Schwegman Lundberg & Woessner, P.A.

(57) ABSTRACT

The present invention discloses a novel bile acid derivatives having substituted nitrogen functionality at C-11 and process for synthesis thereof. These C-11 substituted bile acid derivatives shows anticancer and antimycobacterial activity.

15 Claims, 2 Drawing Sheets

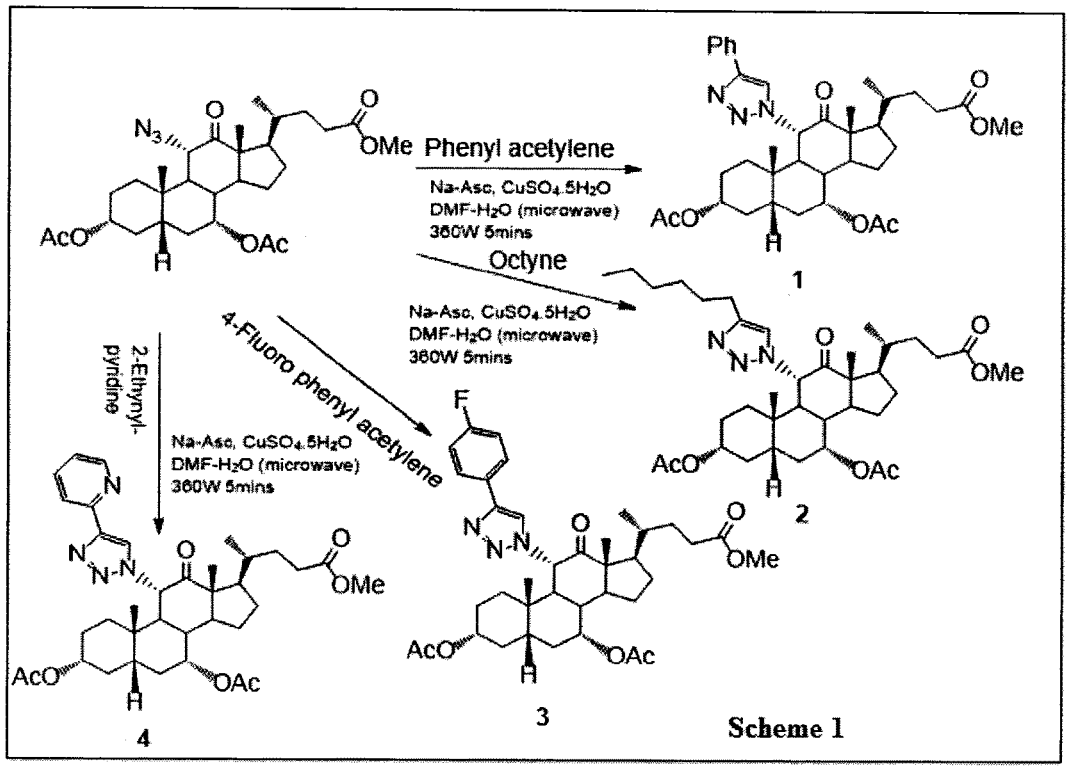
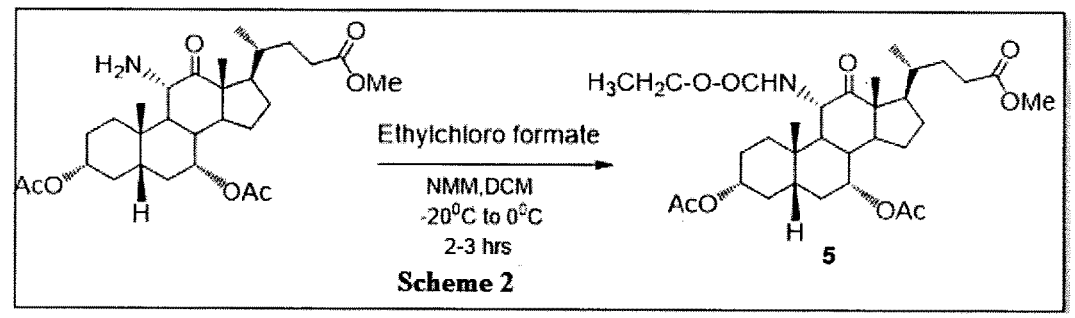
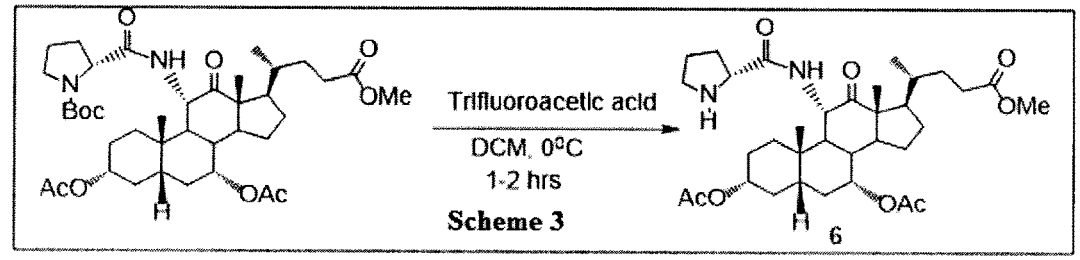
Fig: 1

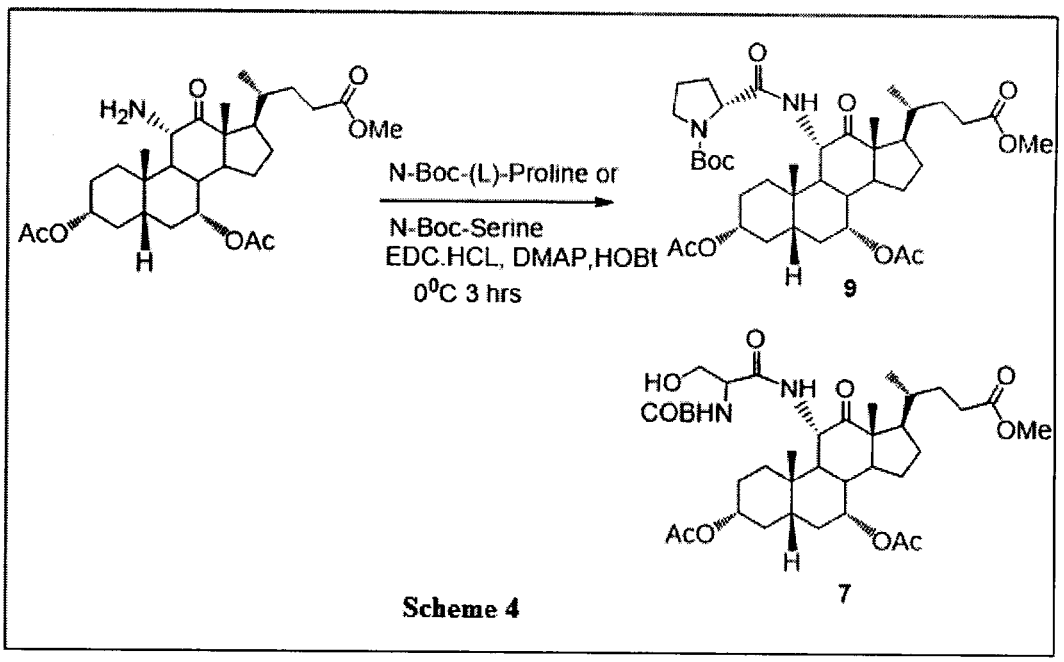
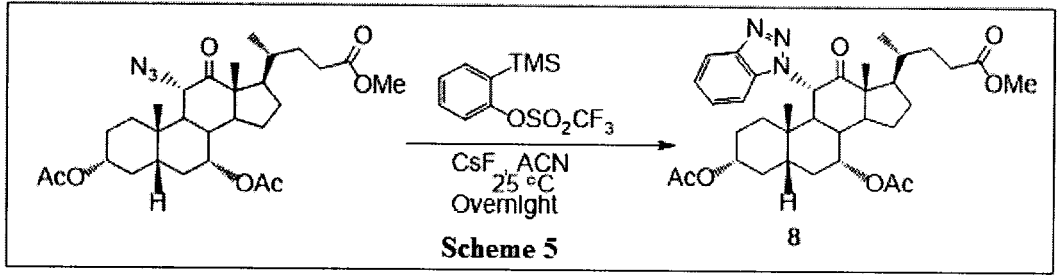
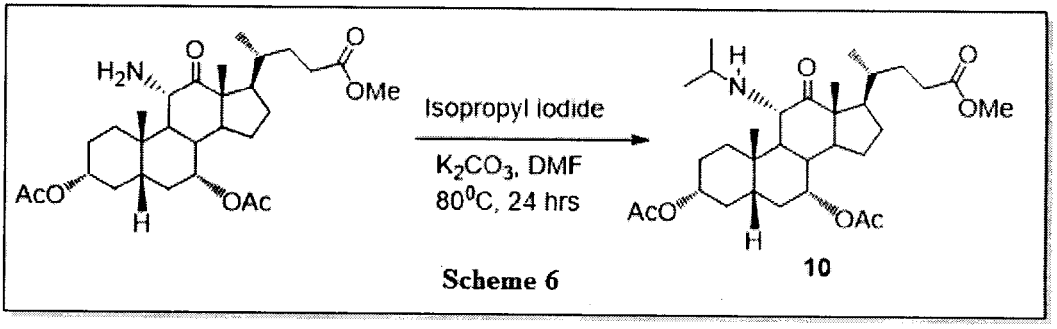
Fig: 2

11-SUBSTITUTED BILE ACID DERIVATIVES, PROCESS FOR THE PREPARATION THEREOF AND USE OF THESE COMPOUNDS AS MEDICAMENTS

PRIORITY CLAIM TO RELATED APPLICATIONS

This application is a U.S. national stage application filed under 35 U.S.C. § 371 from International Application Serial No. PCT/IN2014/000730, which was filed 24 Nov. 2014, and published as WO2015/087340 on 18 Jun. 2015, and which claims priority to Indian Application No. 3619/DEL/2013, filed 12 Dec. 2013, which applications and publication are incorporated by reference as if reproduced herein and made a part hereof in their entirety, and the benefit of priority of each of which is claimed herein.

FIELD OF THE INVENTION

The present invention relates to novel C-11 functionalized bile acid derivatives. More particularly, the present invention relates to novel C-11 functionalized bile acid derivatives, process for preparation thereof and its use as anticancer and antimycobacterial agents.

BACKGROUND AND PRIOR ART

Steroids with C-11 functionality are crucial for biological activity and are observed in a number of drug molecules including steroid hormones. Steroids with C-11 functionality are well-known for biological activity and are obtained in a number of naturally occurring molecules such as cortisone, hydrocortisone, and corticosterone. Potent synthetic corticosteroids such as dexamethasone, triamcinolone, and fluticasone also possess C-11 hydroxy functionality. Stereoselective C-11 functionalization in the steroids is one of the challenging targets for synthetic organic chemists because it involves severe steric interactions due to C-18 and C-19 angular methyl groups. Introduction of the C-11 R-hydroxyl functionality via microbial hydroxylation by the Syntex et al. in *J. Am. Chem. Soc*, 1952, 74, 5933-5936 and via long-range chemical functionalization by Breslow et al. in *Acc. Chem. Res*, 1980, 13, 170-177 is well documented.

PCT application no. 2002014342A1 discloses a series of novel steroid derivatives wherein the steroid derivatives are antibacterial agents. The steroid derivatives also act to sensitize bacteria to other antibiotics including erythromycin and novobiocin. The invention features compounds of the formula I

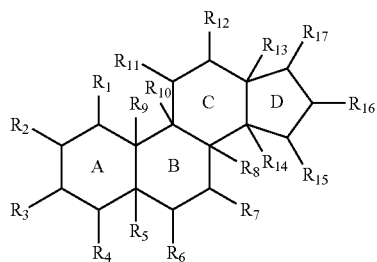

wherein:
fused rings A, B, C, and D are independently saturated or fully or partially unsaturated; and $R_1$ through $R_4$, $R_6$, $R_7$, $R_{11}$, $R_{12}$, $R_{15}$, $R_{16}$, and $R_{17}$ is each independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—$HC(Q_5)$-$C(O)$—$O$—, $H_2N$—$HC(Q_5)$-$C(O)$—$N(H)$—, ($C_1$-$C_{10}$) azidoalkyloxy, ($C_1$-$C_{10}$) cyanoalkyloxy, P.G.-HN—$HC(Q_5)$-$C(O)$—$O$—, ($C_1$-$C_{10}$) guanidinoalkyloxy, ($C_1$-$C_{10}$) quaternaryammonium-alkylcarboxy, and ($C_1$-$C_{10}$) guanidinoalkylcarboxy, where $Q_5$ is a side chain of any amino acid, P.G. is an amino protecting group.

Article titled "An efficient method for the synthesis of methyl 11α-amino-3α,7α-diacetoxy-12-oxo-5b-cholan-24-oate" by D B Salunke et al. published in *Tetrahedron*, Volume 61, Issue 14, 4 Apr. 2005, Pages 3605-3612 reports the synthesis of methyl 11α-azido-3α,7α-diacetoxy-12-oxo-5β-cholan-24-oate, methyl 11β-azido-3α,7α-diacetoxy-12-oxo-5β-cholan-24-oate and methyl 11α-amino-3α,7α-diacetoxy-12-oxo-5β-cholan-24-oate. The assignment of the stereochemistry at C-11 of compound 13 was supported by the 1H NMR spectrum in which the C-11 proton appeared as a doublet (d 4.06 ppm, JZ10.8 Hz) due to trans diaxial coupling between the C-11 and C-9 protons.

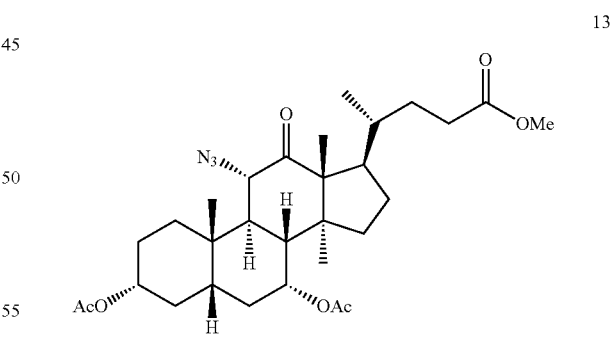

13

Article titled "Amino functionalized novel cholic acid derivatives induce HIV-1 replication and syncytia formation in T cells" by D B Salunke et al. published in *J Med Chem.*, 2006 Apr. 20; 49(8), 2652-2655 reports synthesis of C-11 azido/amino functionalized cholic acid derivatives in excellent yields. Contrary to the previous prediction of analogous compounds to be HIV-1 protease inhibitors, in the present study these novel cholic acid derivatives induced host cell fusion during the progress of HIV-1 infection and produced multinucleated giant cells.

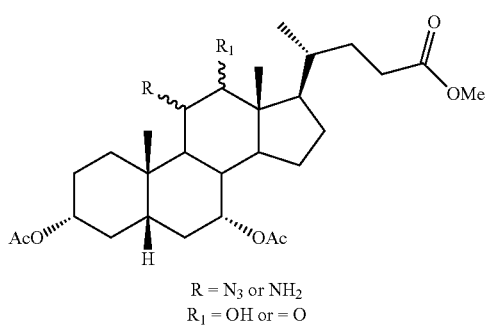

R = N₃ or NH₂
R₁ = OH or = O

Article titled "Synthesis of novel steroidal inhibitors of HIV-1 protease" by Marples et al. published in *Tetrahedron*, Volume 54, Issue 39, 24 Sep. 1998, Pages 11907-11924 reports the design and synthesis of potential steroidal HIV-1 protease inhibitors is described. Compounds derived from 11-amino-12-keto-cholanic acid derivatives show modest activity.

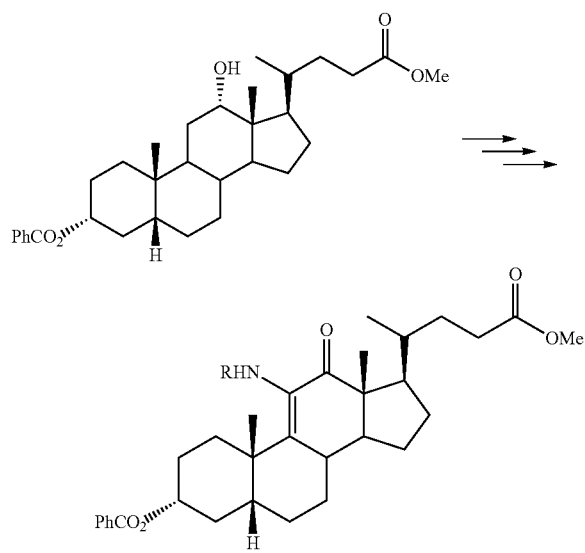

Article titled "Synthesis of bile acid dimers linked with 1,2,3-triazole ring at C-3, C-11, and C-24 Positions" by N G Aher et al. published in Synlett, 2005, 14, pp 2155-2158 reports 1,3-dipolar cycloaddition of propargyl ester of a bile acid to an azide group attached at different positions of another bile acid gave three new 1,2,3-triazole-containing dimeric analogues in excellent yields.

Therefore, there is need in the art to develop C-11 functionalized bile acid derivatives which are easily prepared and used for pharmaceutical purpose. Accordingly, the present invention describes the C-11 functionalized bile acid derivatives which show anticancer and antimicrobial activity.

OBJECTIVE OF INVENTION

The main objective of the present invention is to provide a novel bile acid derivatives having substituted nitrogen functionality at C-11.

Another objective of the present invention is to provide a process for the preparation of novel C-11 functionalized bile acid derivatives.

One more objective of the present invention is to evaluate the anticancer and antimycobacterial activity of these novel C-11 functionalized bile acid derivatives.

SUMMARY OF THE INVENTION

Accordingly, the present invention provides novel C-11 functionalized bile acid derivatives of Formula (I):

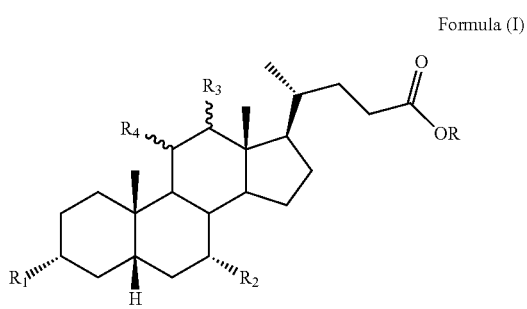

Formula (I)

wherein, R is selected from hydrogen, linear or branched alkyl group;

$R_1$ and $R_2$ are selected from OH, OAc and OBz;

$R_3$ is selected from OH, =O; and $R_4$ is selected from long or short alkyl chain substituted amino group with or without additional amino group, heterocyclic group, amide group, or a pharmaceutically acceptable salt thereof.

In an aspect, the present invention provides a process for the preparation of C-11 functionalized bile acid derivatives from cholic acid.

In another aspect, the present invention provides a pharmaceutical composition comprising an effective amount of a compound of Formula (I).

In yet another aspect, the present invention provides a method of treating cancer by administering to the host an effective amount of a pharmaceutical composition comprising a compound of Formula (I) or a pharmaceutically acceptable salt thereof.

In still another aspect, the present invention provide a method of treating mycobacterial infection of a host by administering to the host an effective amount of an antimycobacterial composition comprising a compound selected from;

2

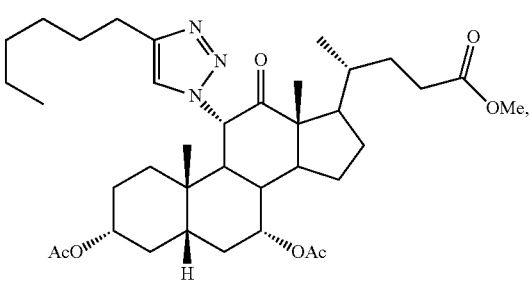

-continued

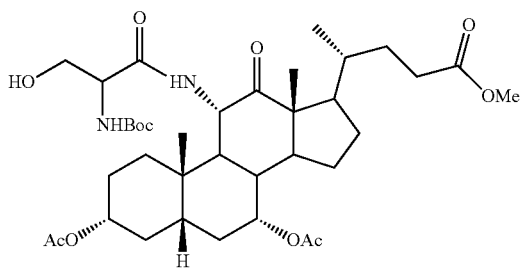

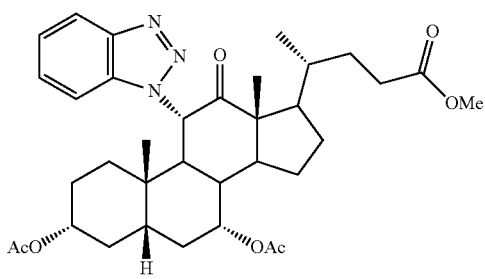

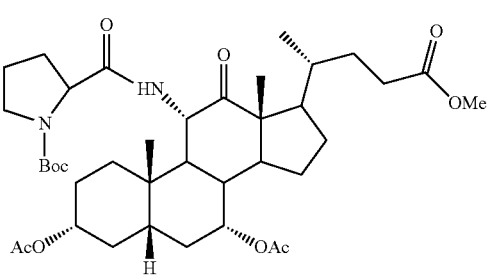

or a pharmaceutically acceptable salt thereof.

BRIEF DESCRIPTION OF THE DRAWINGS

FIG. 1: Scheme 1 depicts coupling of C-11 azide with phenyl acetylene, octyne, 4-fluoro phenyl acetylene and 2-ethynyl pyridine.

FIG. 1: Scheme 2 depicts acylation of C-11 amine with Ethyl hloroformate.

FIG. 1: Scheme 3 depicts deprotection of boc group of proline derivative of diacetyl methyl cholate FIG. 2: Scheme 4 depicts coupling of C-11 amine with N-boc proline and N-boc serine.

FIG. 2: Scheme 5 depicts click reaction between C-11 azide with 2-(trimethylsilyl) phenyl trifluoromethanesulfonate.

FIG. 2: Scheme 6 depicts alkylation of C-11 amine with Isopropyl iodide.

DETAILED DESCRIPTION OF THE INVENTION

The invention will now be described in detail in connection with certain preferred and optional embodiments, so that various aspects thereof may be more fully understood and appreciated.

In an embodiment, the present invention provides novel compounds of Formula (I),

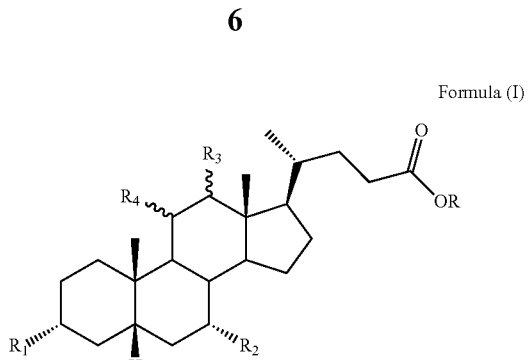

Formula (I)

wherein, R is selected from hydrogen, linear or branched alkyl group;

$R_1$ and $R_2$ are selected from OH, OAc and OBz;

$R_3$ is selected from OH, $=$O; and $R_4$ is selected from long or short alkyl chain substituted amino group with or without additional amino group, heterocyclic group, amide group;

or a pharmaceutically acceptable salt thereof.

In a preferred embodiment, the present invention provides 3,7-diacetoxy or dibenzoyloxy-11-azido-12-oxo methyl cholate for preparation of 1,2,3-triazoles at C-11.

In another preferred embodiment, the present invention provides 3,7-diacetoxy or dibenzoyloxy-11-amino-12-oxo methyl cholate for the preparation of C-11 amino compounds substituted with alkyl, acyl, amide functionality.

The compounds of Formula (I) are preferably selected from,

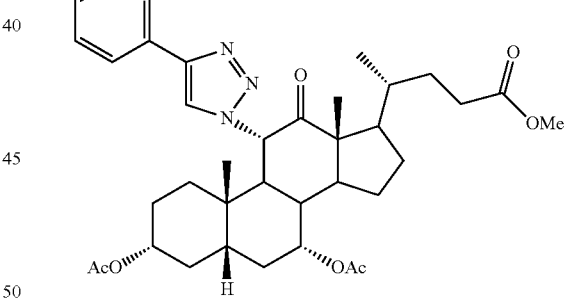

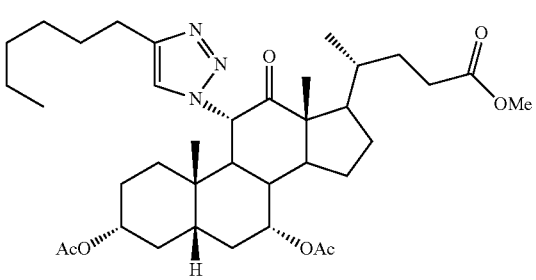

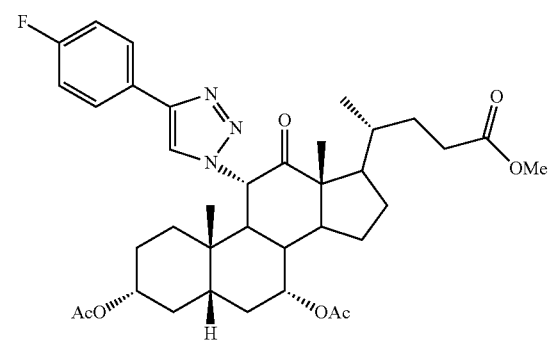

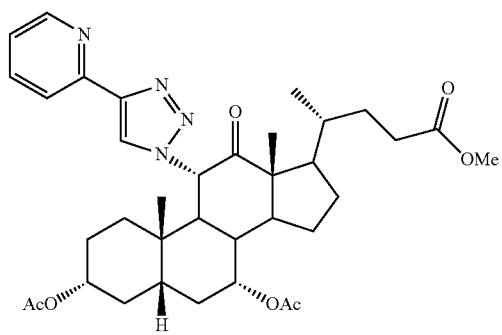

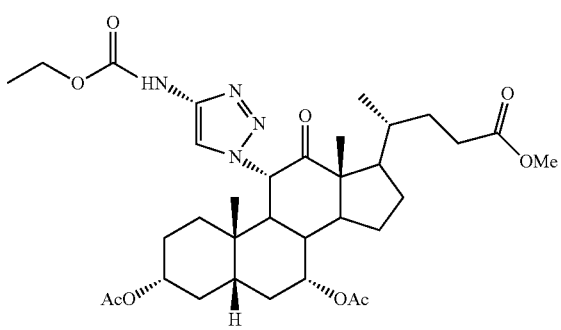

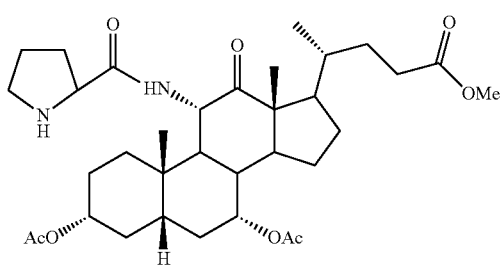

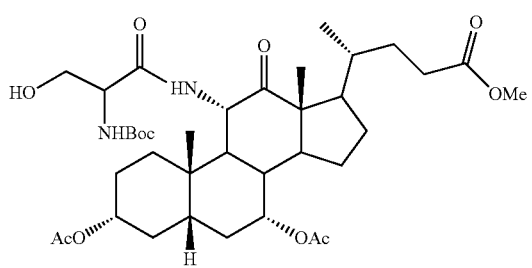

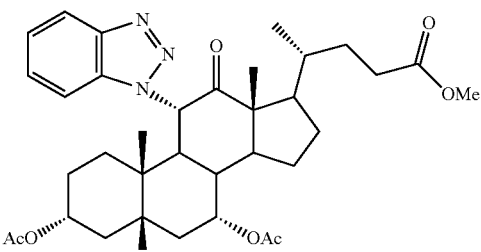

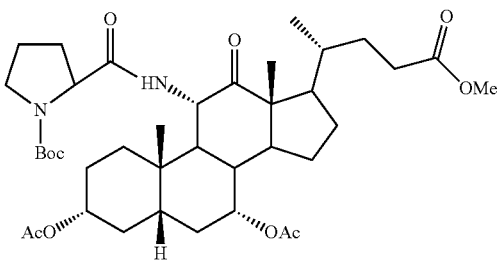

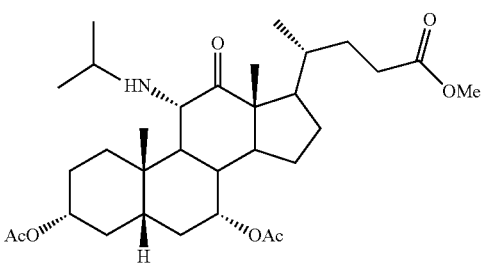

In another embodiment, the present invention provides a process for the preparation of compound of Formula (I) from cholic acid comprising:

a. esterfying cholic acid using methanol in the presence of an acid catalyst and purifying product of reaction to obtain methyl cholate;

b. protecting the hydroxyl groups at C-3 and C-7 of methyl cholate of step (a) as acetates or benzoates by using acetic anhydride or benzoyl chloride to obtain 3,7-diacetoxy or dibenzoyloxy methyl cholate;

c. oxidizing the hydroxyl group at C-12 of methyl cholate of step (b) to obtain 3,7-diacetoxy or dibenzoyloxy-12-oxo methyl cholate;

d. brominating 3,7-diacetoxy or dibenzoyloxy-12-oxo methyl cholate of step (c) using bromine in benzene to obtain 3,7-diacetoxy or dibenzoyloxy-11-bromo-12-oxo methyl cholate;

e. substituting the bromo group in 3,7-diacetoxy or dibenzoyloxy-11-bromo-12-oxo methyl cholate of step (d) using sodium azide in DMF solvent to obtain 3,7-diacetoxy or dibenzoyloxy-11-azido-12-oxo methyl cholate; and f. alkylating, acylating or coupling of different amino acids, alkynyl compounds with compound of step (e) or reduction compound of step (e) to give compound of Formula (I);

wherein, the process optionally comprises reduction of azido group in 3,7-diacetoxy or dibenzoyloxy-11-azido-12-oxo methyl cholate of step (e) using triphenyl phosphine followed by reaction with water to obtain 3,7-diacetoxy or dibenzoxy-11-amino-12-oxo methyl cholate.

In still another embodiment, the present invention provide salts of C-11 functionalized bile acid derivatives of Formula (I) by hydrolysis of the ester functionality at C-24 position with alkali or alkaline earth metal hydroxide to get the salt of C-11 functionalized bile acid derivatives.

The process for the preparation of compound of Formula (I), is shown below in Scheme 1:

In a preferred embodiment, the invention provides a procedure wherein amino group in 3,7-diacetoxy or dibenzoyloxy-11-amino-12-oxo methyl cholate is alkylated using different short and long chain alkyl halides with or without containing amino functionality comprising:

a. adding anhydrous potassium carbonate to a solution of 3,7-diacetoxy or dibenzoyloxy-11-amino-12-oxo Scheme 1:

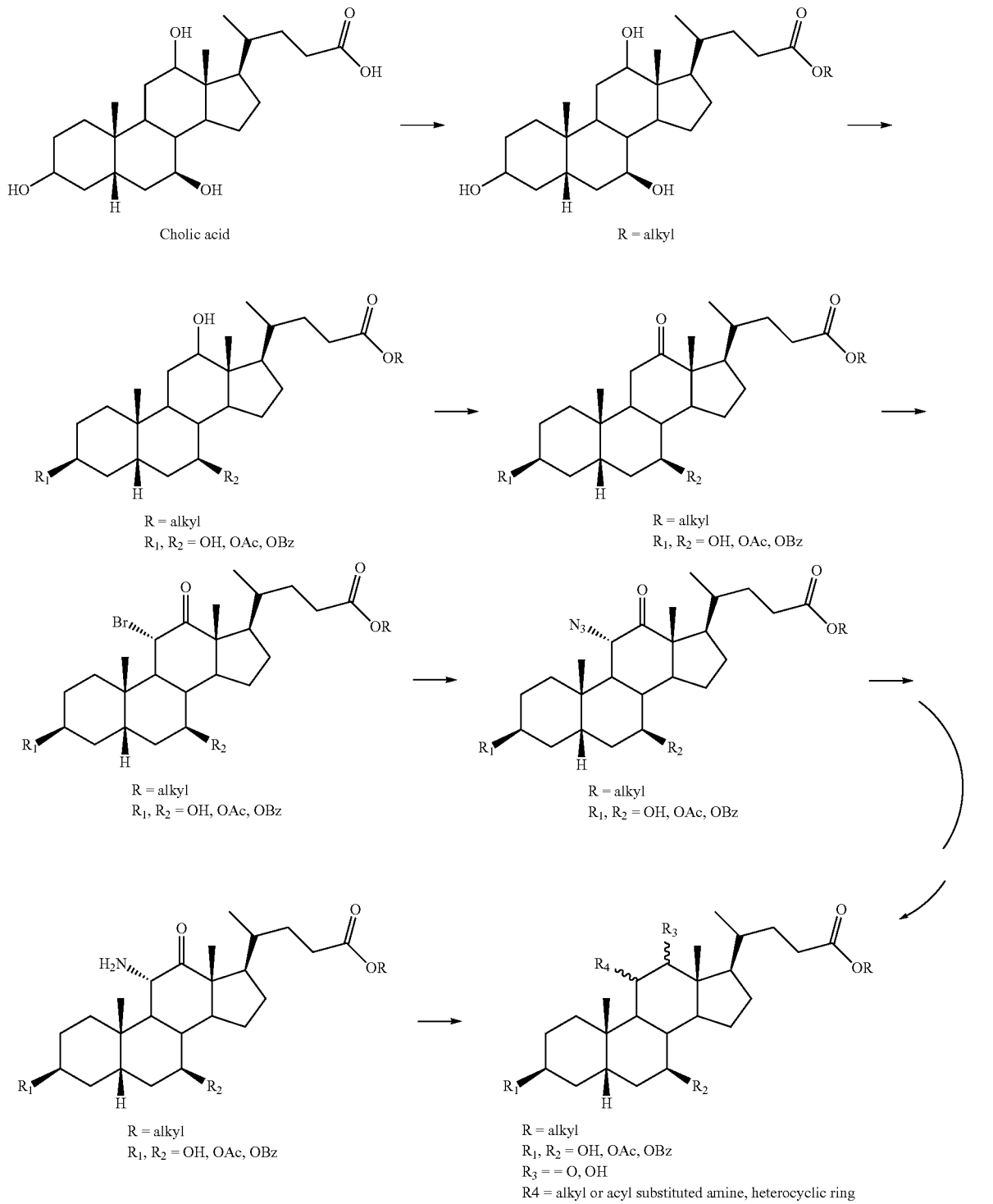

methyl cholate in anhydrous dimethylformamide (DMF) to obtain a mixture;
b. adding alkyl halide to the mixture of step (a) to obtain a reaction mixture; and
c. stirring the reaction mixture of step (b) followed by work-up afforded the desired pure product.

In another preferred embodiment, the invention provides a procedure wherein amino group in 3,7-diacetoxy or dibenzoyloxy-11-amino-12-oxo methyl cholate is acylated using different short and long chain alkyl chloroformates comprising:
a. adding N-methylmorpholine to a solution of 3,7-diacetoxy or dibenzoyloxy-11-amino-12-oxo methyl cholate in anhydrous dichloromethane ($CH_2Cl_2$) and cooling followed by addition of alkyl chloroformate to obtain a reaction mixture; and
b. stirring the reaction mixture of step (a) followed by work-up afforded the desired pure product.

In yet another preferred embodiment, the invention provides a procedure wherein amino group in 3,7-diacetoxy or dibenzoyloxy-11-amino-12-oxo methyl cholate is coupled with different amino acids comprising:
a. adding 1-Ethyl-3-(3-dimethylaminopropyl) carbodiimide (EDC), hydroxylbenzo-triazoleanddimethylaminopyridine (DMAP) to a solution of N-Boc protected amino acid in anhydrous DMF and cooling to obtain a mixture;
b. adding dimethylformamide (DMF) solution of 3,7-diacetoxy or dibenzoyloxy-11-amino-12-oxo methyl cholate to the mixture of step (a) to obtain a reaction mixture; and
c. stirring the reaction mixture of step (b) followed by work-up afforded the desired pure product.

In still another preferred embodiment, the invention provides a procedure wherein azido group in 3,7-diacetoxy or dibenzoyloxy-11-azido-12-oxo methyl cholate is coupled with different alkynyl compounds to give 1,4-disubstituted-1,2,3-triazole ring at C-11 comprising:
a. dissolving 3,7-diacetoxy or dibenzoyloxy-11-azido-12-oxo methyl cholate and an alkyne preferably selected from 1-octyne, phenyl acetylene, 4-fluorophenyl acetylene, 2-ethynyl pyridine in $DMF/H_2O$ followed by addition of $CuSO_4.5H_2O$ and sodium ascorbate to obtain a reaction mixture; and
b. irradiating the reaction mixture in microwave followed by work-up afforded the desired pure product.

In one embodiment, a pharmaceutical composition is provided comprising a compound of Formula (I), or a stereoisomer, or ester or pharmaceutically acceptable salt thereof, and a pharmaceutically acceptable carrier, diluent or excipient.

The invention encompasses all stereoisomers and enantiomers of compounds of Formula (I). The invention further encompasses pharmaceutical salts of the compound of Formula (I), such as acid addition salts of mineral acids, carboxylic acids and sulfonic acids, for example salts of hydrochloric acid, hydrobromic acid, nitric acid, sulfuric acid, phosphoric acid, benzenesulfonicacid, methanesulfonic acid, ethanesulfonic acid, toluenesulfonic acid, formamidinesulfonic acid, naphthalenedisulfonic acid, formic acid, fumaric acid, acetic acid, propionic acid, lactic acid, malic acid, citric acid, maleic acid, benzoic acid, malonic acid, tartaric acid, oxalic acid and succinic acid.

The pharmaceutically acceptable salts further include salts of customary bases, such as for example alkali metal salts (for example sodium and potassium salts), alkaline earth metal salts (for example calcium and magnesium salts), and ammonium salts derived from ammonia or organic amines.

The compound of Formula (I) disclosed herein is present in the composition in an amount which may be effective to treat the disease or the condition caused by the bacterial strains mentioned above. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres.

The compound of Formula (I) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

The pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

As mentioned above, the present invention provides a pharmaceutical formulation having an effective amount of a compound of Formula (I) for treating a patient having a bacterial infection. The compounds may find further uses in other therapeutic areas selected from, but not limited to such as anti-bacterial, anti-mycobacterial and anti-malarial.

As used herein, an effective amount of the compound is defined as the amount of the compound which, upon administration to a patient, inhibits growth of bacteria, kills bacteria cells, sensitizes bacteria to other antibiotics, or eliminates the bacterial infection entirely in the treated patient. The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01-1 mg/kg/day, is generally sufficient. Effective doses will also vary, as recognized by those skilled in the art, dependent on route of administration, excipient usage, and the possibility of co-usage with other therapeutic treatments including other antibiotic agents.

In an embodiment, the present invention provide a method of treating cancer by administering to the host an effective amount of an pharmaceutical composition comprising a compound according to Formula (I):

Formula (I)

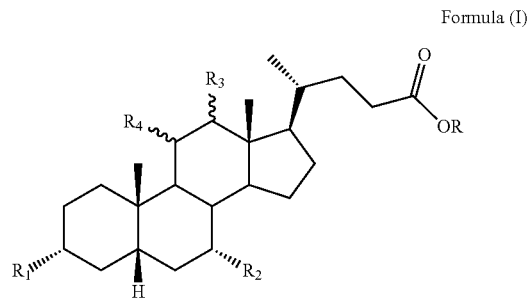

wherein, R is selected from hydrogen, linear or branched alkyl group;

$R_1$ and $R_2$ are selected from OH, OAc, OBz;

$R_3$ is selected from OH, =O; and $R_4$ is selected from long or short alkyl chain substituted amino group with or without additional amino group, heterocyclic group, amide group; or a pharmaceutically acceptable salt thereof wherein the cancer is human cervix epithelioid carcinoma cell line cancer.

The host disclosed in the present invention is a human.

In yet another embodiment of the present invention a method of treating cancer by administering to the host an effective amount of an pharmaceutical composition comprising compounds preferably selected from;

1
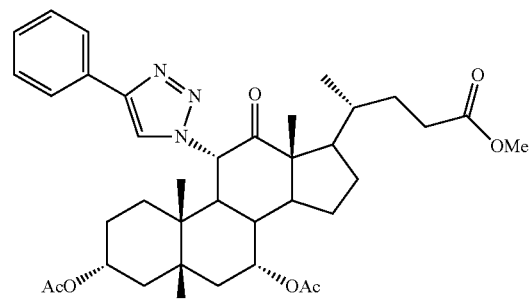

2
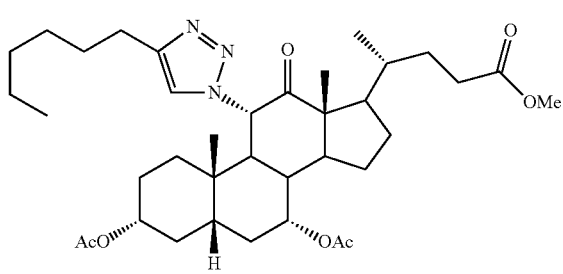

3
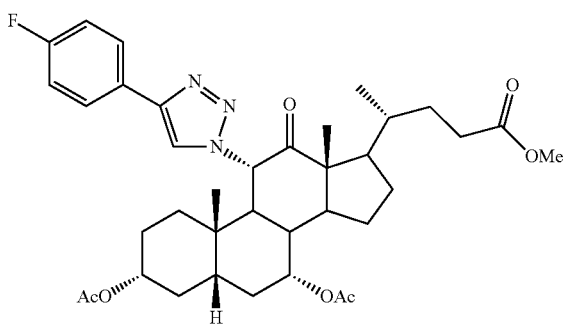

4
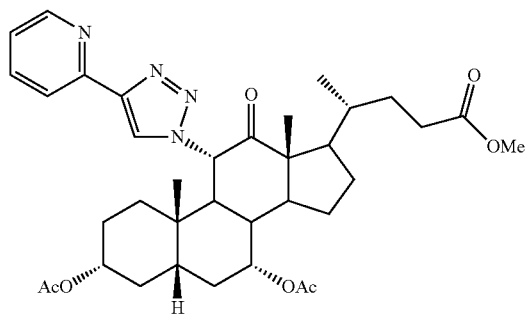

5
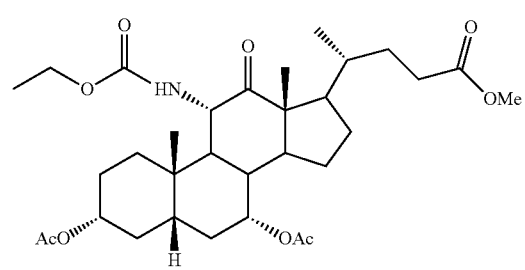

6
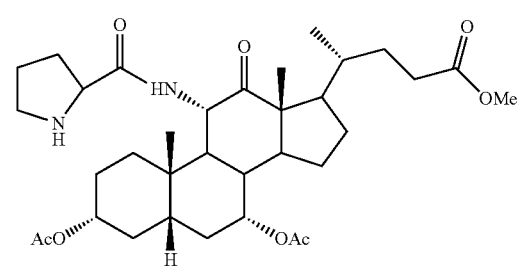

7
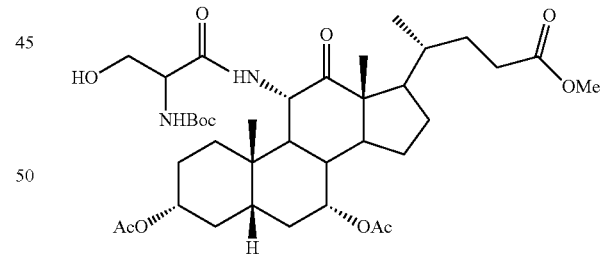

8
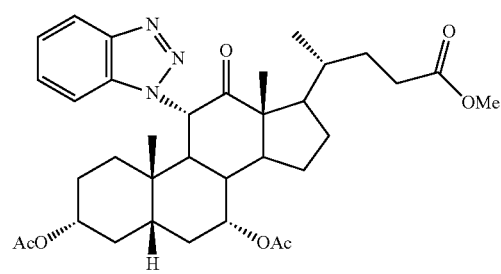

-continued

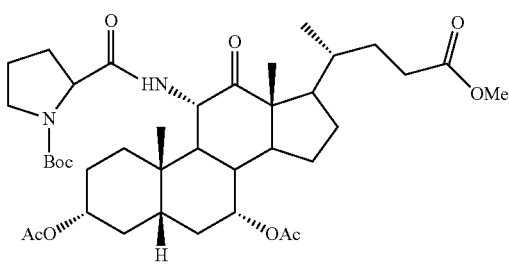

9

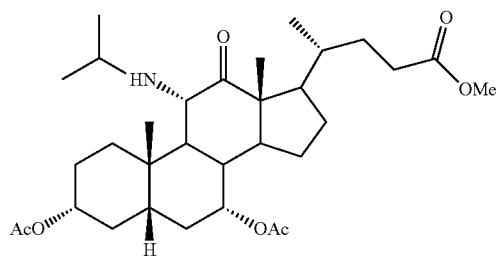

10

These compounds show good activity against human cervix epithelioid carcinoma cell line. The anti-cancer screening results of synthesized compounds (1 to 10) and their IC50 and MIC values against human cancer cell lines are described in Table 1.

In an embodiment, the present invention provides a method of treating which the host is a human.

In another embodiment, the present invention provide a method of treating mycobacterial infection of a host by administering to the host an effective amount of an antimycobacterial composition comprising a compound selected from;

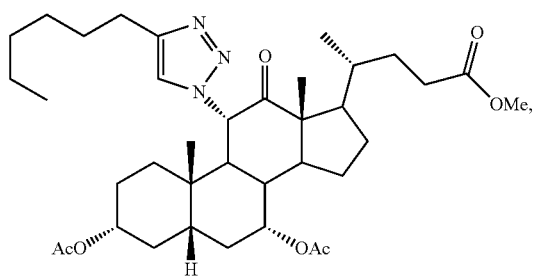

2

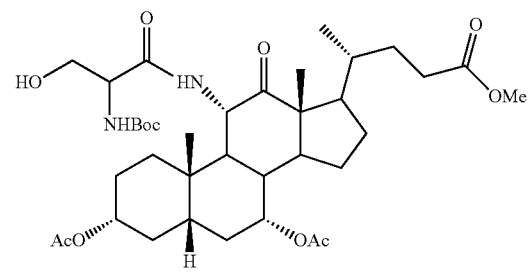

7

-continued

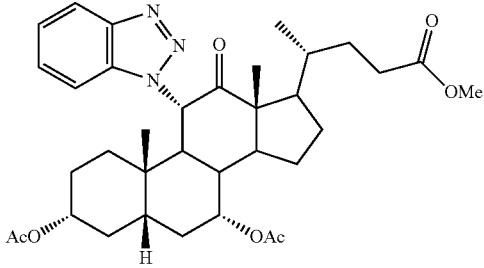

8

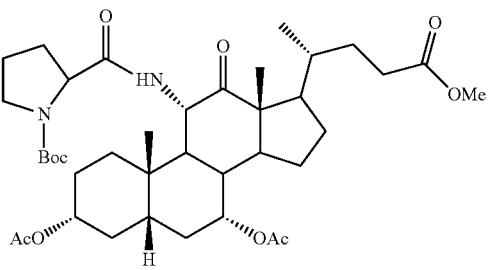

9 or a pharmaceutically acceptable salt thereof, wherein the mycobacterial infection is caused by bacterial species selected from *Mycobacterium tuberculosis* H37Ra or *Mycobacterium Bovis* BCG.

These above four compounds show good antimicobacterial/anti-tuberculosis activity. The anti-tuberculosis IC 50 and MIC chart in vitro and ex-vivo data is summarized in Table 2.

The following examples, which include preferred embodiments, will serve to illustrate the practice of this invention, it being understood that the particulars shown are by way of example and for purpose of illustrative discussion of preferred embodiments of the invention.

EXAMPLES

Following examples are given by way of illustration therefore should not be construed to limit the scope of the invention.

Example 1

A) Synthesis of Methyl 3α,7α,12α-trihydroxy-5β-cholane-24-oate

To a solution of cholic acid (0.3 g, 0.74 mmol) in dry methanol (10 mL) was added p-TSA (0.03 g, 0.17 mmol). The mixture was stirred at 28° C. for 24 hrs. Methanol was evaporated and the residue was extracted with $CH_2Cl_2$ (3×50 mL). The organic extract was washed with cold $H_2O$ (2×10 mL), 10% $NaHCO_3$ (2×10 mL), brine (2×10 mL) and dried over $Na_2SO_4$. Solvent was evaporated under reduced pressure to afford crude product. Purification by column chromatography on silica gel (5%, MeOH/$CHCl_3$) afforded compound methyl 3α,7α,12α-trihydroxy-5β-cholane-24-oate. (0.3 g, 98%) as a white solid. mp 155-156° C.; $[α]_D^{28}$+31.33 ($CHCl_3$, c 1.0); IR ($cm^{-1}$): 3376, 1731; $^1$H NMR ($CDCl_3$, 200 MHz): δ 0.68 (s, 3H, $CH_3$-18), 0.89 (s, 3H, $CH_3$-19), 0.98 (d, J=5.7 Hz, 3H, $CH_3$-21), 3.57 (m, 1H CH-3), 3.67 (s, 3H) 3.89 (bs, 1H, CH-7), 4.01 (bs, 1H, CH-12); $^{13}$C NMR ($CDCl_3$, 50 MHz): δ 12.8, 17.7, 22.8, 23.6, 26.6, 27.7, 28.5, 30.0, 31.4, 31.5, 35.2, 35.2, 35.7, 35.8, 39.9, 39.9, 42.0, 42.0, 46.8, 47.3, 51.8, 68.8, 72.2, 73.4, 175.2.

B) Synthesis of Methyl 3α,7α-diacetoxy-12α-hydroxy-5β-cholan-24-oate

To a solution of methyl 3α,7α,12α-trihydroxy-5β-cholane-24-oate (0.211 g, 0.5 mmol), DMAP (0.07 g, 0.06 mmol) and acetic anhydride (0.11 g, 1.05 mmol) in dry $CH_2Cl_2$ (10 mL) was added $Et_3N$ (0.22 g, 2.13 mmol) at 0° C. The reaction mixture was allowed to stir at 0-28° C. for 4-5 hrs, ice cooled water was added to the reaction mixture and it was extracted with $CH_2Cl_2$ (3×50 mL). The organic extract was washed with cold $H_2O$ (2×10 mL), 5% aq. HCl (2×10 mL), 10% $NaHCO_3$ (2×10 mL), brine (2×10 mL) and dried over $Na_2SO_4$. Solvent was evaporated under reduced pressure to afford crude product. Purification by column chromatography on silica gel (25%, EtOAc/PE) afforded methyl 3α,7α-diacetoxy-12α-hydroxy-5β-cholan-24-oate (0.232 g, 92%) as a white crystalline solid. mp 185-188° C.; $[\alpha]_D^{28}$+20.78 (CHCl$_3$, c 0.56); IR (cm$^{-1}$) 3678, 1746, 1735; $^1$H NMR (200 MHz, CDCl$_3$) δ 0.66 (s, 3H), 0.90 (s, 3H), 0.95 (d, J=6.0 Hz, 3H), 2.02 (s, 3H), 2.04 (s, 3H), 3.64 (s, 3H), 3.98 (bs, 1H), 4.56 (m, 1H), 4.87 (bs, 1H); $^{13}$C NMR (50 MHz, CDCl$_3$) δ 12.4, 17.2, 21.3, 21.4, 22.8, 22.9, 26.6, 27.2, 27.8, 28.4, 31.0, 31.2, 34.5, 34.7, 34.8, 35.0, 38.0, 40.9, 42.0, 46.5, 47.6, 51.3, 70.8, 72.5, 74.0, 170.5, 174.5.

C) Synthesis of Methyl 3α,7α-diacetoxy-12-oxo-5β-cholan-24-oate

To a solution of methyl 3α,7α-diacetoxy-12α-hydroxy-5β-cholan-24-oate (0.506 g, 1 mmol) in acetone (20 mL), Jones Reagent (1 mL) was added at 5-10° C. The reaction mixture was stirred at this temperature for 5 min. Methanol (5 mL) was added, the solvent was evaporated and the crude solid material was dissolved in EtOAc/H$_2$O (5:1) mixture (100 mL). The organic layer was washed with cold H$_2$O (2×10 mL), 10% NaHCO$_3$ (2×10 mL), brine (2×10 mL) and dried over Na$_2$SO$_4$. Solvent was evaporated under reduced pressure to afford crude product. Purification by column chromatography on silica gel (20%, EtOAc/PE) afforded pure C-12 oxo compound (0.49 g, 98%) as a white crystalline solid. mp. 175-176° C.; IR (cm-1) 1737, 1730, 1701; $^1$H NMR (300 MHz, CDCl$_3$) δ 0.86 (d, J=5.8 Hz, 3H), 1.03 (s, 3H), 1.04 (s 3H), 2.02 (s, 3H), 2.03 (s, 3H), 2.52 (t, J=12 Hz, 1H), 3.66 (s, 3H), 4.57 (m, 1H), 4.98 (bs, 1H); $^{13}$C NMR (75 MHz, CDCl$_3$) δ 11.4, 18.4, 21.0, 22.0, 23.6, 26.5, 27.7, 30.2, 31.1, 31.2, 34.3, 34.4, 35.4, 37.7, 37.8, 40.5, 46.4, 51.2, 53.0, 57.0, 70.4, 73.4, 169.4, 170.3, 174.2, 213.3; Anal. Calcd. for C$_{29}$H$_{44}$O$_7$: C, 69.02; H, 8.79. Found: C, 69.34; H, 8.57; MS (LCMS) m/z: 527.3 (M+23 for Na).

D) Synthesis of Methyl 11α-bromo-3α,7α-diacetoxy-12-oxo-5β-cholan-24-oate

To a solution of methyl 3α,7α-diacetoxy-12-oxo-5β-cholan-24-oate (1.008 g, 2 mmol) in benzene (10 mL), bromine solution (1 mL, 2M in benzene) was slowly added with stirring, at 30° C. in the dark. After 6 days, TLC analysis showed the total consumption of the starting material. The solvent was evaporated and the crude solid material was dissolved in EtOAc (150 mL). The organic layer was washed with 10% Na$_2$S$_2$O$_5$ (2×10 mL), cold H$_2$O (2×10 mL), brine (2×10 mL) and dried over Na$_2$SO$_4$. Solvent was evaporated under reduced pressure to afford crude product. The residue was chromatographed on flash silica gel (10%, EtOAc/PE) to yield the methyl 11α-bromo-3α,7α-diacetoxy-12-oxo-5β-cholan-24-oate (0.76 g, 65%). mp. 183-184° C.; $[\alpha]_D^{25}$+19.20 (CHCl$_3$, c 1.25); IR (cm-1) 2937, 1739, 1730, 1697; $^1$H NMR (200 MHz, CDCl$_3$) δ 0.93 (d, J=6.6 Hz, 3H), 1.36 (s, 3H), 1.38 (s, 3H), 2.03 (s, 6H), 2.64 (dd, J=11.7 & 5.9 Hz, 1H), 3.67 (s, 3H), 4.42 (d, J=5.9 Hz, 1H), 4.60 (m, 1H), 5.03 (bs, 1H); $^{13}$C NMR (50 MHz, CDCl$_3$) δ 15.5, 18.1, 21.1, 21.2, 23.7, 24.6, 26.9, 27.3, 30.4, 30.6, 31.1, 33.7, 34.6, 35.6, 35.8, 36.9, 39.9, 43.8, 47.4, 51.3, 52.0, 52.2, 56.3, 70.6, 73.1, 169.6, 170.3, 174.3, 203.4; MS (LCMS) m/z 605.2 (M+23 for Na).

E) Synthesis of Methyl 11α-azido-3α,7α-diacetoxy-12-oxo-5β-cholan-24-oate

To a solution of methyl 11α-bromo-3α,7α-diacetoxy-12-oxo-5β-cholan-24-oate (0.1 g, 0.172 mmol) in dry DMF (5 mL) was added solid sodium azide (0.056 g, 0.86 mmol). The reaction mixture was stirred at 60° C. for 16 h and allowed to cool to room temperature. It was then poured into H$_2$O (50 mL) and extracted with Et$_2$O (3×50 mL). The organic extract was washed with cold water (2×25 mL) followed by brine (20 mL) and it was dried over Na$_2$SO$_4$. Solvent was evaporated under reduced pressure to afford crude product. Purification by column chromatography on silica gel (10% EtOAc/PE) afforded methyl 11α-azido-3α,7α-diacetoxy-12-oxo-5β-cholan-24-oate (0.092 g, 98%) as a white crystalline solid. mp. 213° C.; $[\alpha]_D^{28}$+61.68 (CHCl$_3$, c 1.07); IR (cm$^{-1}$) 2922, 2108, 1740, 1722; $^1$H NMR (200 MHz, CDCl$_3$) δ 0.88 (d, J=6.4 Hz, 3H), 1.02 (s, 3H), 1.15 (s, 3H), 2.02 (s, 3H), 2.04 (s, 3H), 2.48 (dt, J=14.6 Hz & 3.0 Hz, 1H), 3.66 (s, 3H), 4.06 (d, J=10.8 Hz, 1H), 4.58 (m, 1H), 4.96 (bs, 1H); $^{13}$C NMR (50 MHz, CDCl$_3$) δ 10.7, 18.3, 21.2, 21.2, 22.7, 23.9, 27.0, 27.4, 30.1, 30.9, 31.4, 35.2, 35.2, 37.0, 37.2, 37.9, 41.6, 42.9, 47.0, 51.3, 51.7, 56.1, 64.4, 70.4, 73.4, 169.8, 170.6, 174.1, 207.0; Anal. Calcd. for C$_{29}$H$_{43}$N$_3$O$_7$ C, 63.81; H, 7.96; N, 7.70. Found: C, 63.68; H, 7.91; N, 7.63.

F) Synthesis of Methyl 11α-amino-3α,7α-diacetoxy-12-oxo-5β-cholan-24-oate

Method A: Methyl 11α-azido-3α,7α-diacetoxy-12-oxo-5β-cholan-24-oate (0.25 g, 0.46 mmol) in EtOAc (15 mL) was hydrogenated at 28° C. and 40 psi pressure using 10% Pd/C (0.025 g) for 5 h. After filtration of the catalyst and evaporation of the solvent, afforded methyl 11α-amino-3α,7α-diacetoxy-12-oxo-5β-cholan-24-oate (0.224 g, 95%) as white solid. Method B: A solution of methyl 11α-azido-3α,7α-diacetoxy-12-oxo-5β-cholan-24-oate (0.11 g, 0.2 mmol) was stirred with triphenylphosphine (0.08 g, 0.3 mmol) in dry THF (5 mL) for 24 h. Water (0.1 mL) was added and the solvent was removed after additional 24 h. After dilution with EtOAc (100 mL), the organic layer was separated, washed with water (2×20 mL), brine (20 mL), dried and solvent was evaporated under reduced pressure. Chromatography of the residue on alumina (10% EtOAc/PE) afforded Methyl 11α-amino-3α,7α-diacetoxy-12-oxo-5β-cholan-24-oate (0.08 g, 80%) as white solid. Mp. 154° C. (EtOAc/PE); $[\alpha]_D^{28}$+61.84 (c 1.52, CHCl$_3$); IR $\nu_{max}$ (Nujol) 3389, 2954, 1731, 1714 cm$^{-1}$; $^1$H NMR (500 MHz, CDCl$_3$) δ 0.85 (d, J=6.5 Hz, 3H), 1.01 (s, 3H), 1.19 (s, 3H), 2.01 (s, 3H), 2.02 (s, 3H), 2.27 (m, 1H), 2.40 (m, 1H), 2.72 (dt, J=14.1 Hz & 3.0 Hz, 1H), 3.66 (s, 3H), 3.76 (d, J=10.0 Hz, 1H), 4.64 (m, 1H), 4.94 (bs, 1H); $^{13}$C NMR (125 MHz, CDCl$_3$) δ 11.0, 18.5, 21.4, 21.4, 23.1, 24.3, 27.4, 28.0, 30.4, 31.2, 31.8, 35.4, 35.4, 37.6, 37.8, 38.5, 42.2, 46.0, 47.3, 51.4, 52.3, 56.0, 57.0, 71.0, 74.0, 170.1, 170.6, 174.5, 214.1; MS (LCMS) m/z 520.03 [M+H]$^+$; Anal calcd. for $C_{29}H_{45}NO_7$ C, 67.01; H, 8.74; N, 2.69. Found: C, 66.77; H, 9.14; N, 2.72.

Example 2

Synthesis of (3R,5S,7R,10S,11S,13R)-17-((R)-5-methoxy-5-oxopentan-2-yl)-10,13-dimethyl-12-oxo-11-(4-phenyl-1H-1,2,3-triazol-1-yl)hexadecahydro-1H-cyclopenta[a]phenanthrene-3,7-diyl diacetate (Compound 1)

Phenyl acetylene (0.030 g, 0.29 mmol) and the azide (0.1 g, 0.18 mmol) were dissolved in DMF:H$_2$O (4:1) 5 mL. To this solution CuSO$_4$.5H$_2$O (0.002 g, 0.01 mmol) and sodium ascorbate (0.015 g, 0.08 mmol) were added. The reaction mixture was placed in domestic microwave reactor and irradiated for 5 min. at 360 W. The reaction mixture was cooled, diluted with cold water and then extracted with EtOAc. Organic phase was dried over anhydrous Na$_2$SO$_4$. Solvent was evaporated under reduced pressure and crude product purified by column chromatography on silica gel using Ethyl acetate/hexane (1:4) to get the pure product 1. Colorless solid, Yield: 71%; $^1$H NMR (200 MHz, CDCl$_3$): δ 7.96 (s, 1H), 7.85 (d, 2H), 7.42 (t, 2H), 7.33 (t, 1H), 5.02 (s, 1H), 4.31 (m, 1H), 3.64 (s, 3H), 2.08 (s, 1H), 1.96 (s, 1H), 1.29 (s, 3H), 1.24 (s, 3H), 1.20 (s, 3H), 0.73 (d, 3H).

Example 3

Synthesis of (3R,5S,7R,10S,11S,13R)-11-(4-hexyl-1H-1,2,3-triazol-1-yl)-17-((R)-5-methoxy-5-oxopentan-2-yl)-10,13-dimethyl-12-oxohexadecahydro-1H-cyclopenta[a]phenanthrene-3,7-diyl diacetate (Compound 2)

Octyne (0.024 g, 0.23 mmol) and the azide (0.079 g, 0.15 mmol) were dissolved in DMF:H$_2$O (1:0.2) ml. To this solution CuSO$_4$.5H$_2$O (0.002 g, 0.01 mmol) and sodium ascorbate (0.012 g, 0.0.06 mmol) were added. The reaction mixture was placed in domestic microwave reactor and irradiated for 10 min. at 360 W. The reaction mixture extracted with EtOAc. Solvent was evaporated under reduced pressure and crude product purified by column chromatography on silica gel using 25% EtOAc: Pet Ether to get pure compound 2 as colourless solid. Yield: 31.58%; $^1$H NMR (200 MHz, CDCl$_3$): δ 7.48 (s, 1H), 5.86 (s, 1H), 5.02 (s, 1H), 4.42 (m, 1H), 3.66 (s, 3H), 2.75 (t, 2H), 2.08 (s, 3H), 1.99 (s, 3H), 1.27 (s, 3H), 1.26 (s, 3H), 1.18 (s, 3H), 0.89 (s, 3H).

Example 4

Synthesis of (3R,5S,7R,10S,11S,13R)-11-(4-(4-fluorophenyl)-1H-1,2,3-triazol-1-yl)-17-((R)-5-methoxy-5-oxopentan-2-yl)-10,13-dimethyl-12-oxo-hexadecahydro-1H-cyclopenta[a]phenanthrene-3,7-diyl diacetate (Compound 3)

4-Fluoro Phenyl acetylene (0.033 g, 0.28 mmol) and the azide 0.1 g, 0.18 mmol) were dissolved in DMF:H$_2$O (1:0.2) ml. To this solution CuSO$_4$.5H$_2$O (0.002 g, 0.01 mmol) and sodium ascorbate (0.015 g, 0.0.08 mmol) were added. The reaction mixture was placed in domestic microwave reactor and irradiated for 5 min. at 360 W. The reaction mixture extracted with EtOAc. Solvent was evaporated under reduced pressure and crude product purified by column chromatography on silica gel using 25% EtOAc: Pet Ether to get pure Compound 3 as colorless solid. Yield: 81%; $^1$H NMR (200 MHz, CDCl$_3$): δ 7.93 (s, 1H), 7.81 (three d, 2H), 7.12 (three d, 2H), 5.91 (d, 1H), 5.03 (d, 1H), 4.40 (m, 1H), 3.66 (s, 3H), 2.09 (s, 3H), 1.97 (s, 3H), 1.30 (s, 3H), 1.26 (s, 3H), 1.21 (s, 3H), 0.76 (d, 3H).

Example 5

Synthesis of (3R,5S,7R,10S,11S,13R)-17-((R)-5-methoxy-5-oxopentan-2-yl)-10,13-dimethyl-12-oxo-11-(4-(pyridin-2-yl)-1H-1,2,3-triazol-1-yl)hexadecahydro-1H-cyclopenta[a]phenanthrene-3,7-diyl diacetate (Compound 4)

2-Ethynyl pyridine (0.028 g, 0.27 mmol) and the azide (0.1 g, 0.18 mmol) were dissolved in DMF:H$_2$O (1:0.2) ml. To this solution CuSO$_4$.5H$_2$O (0.002 g, 0.01 mmol) and sodium ascorbate (0.015 g, 0.0.08 mmol) were added. The reaction mixture was placed in domestic microwave reactor and irradiated for 5 min. at 360 W. The reaction mixture extracted with EtOAc. Solvent was evaporated under reduced pressure and crude product purified by column chromatography on silica gel using 25% EtOAc: Pet Ether to get pure Compound 4 as colorless solid. Yield: 87%; $^1$H NMR (200 MHz, CDCl3): δ 8.59 (d, 1H), 8.39 (s, 1H), 8.22 (d, 1H), 7.81 (t, 1H), 5.05 (d, 1H), 4.38 (m, 1H), 3.65 (s, 3H), 2.11 (s, 3H), 1.94 (s, 3H), 1.32 (s, 3H), 1.26 (s, 3H), 1.19 (s, 3H), 0.75 (d, 3H).

Example 6

Synthesis of (3R,5S,7R,10S,11S,13R)-11-((ethoxycarbonyl)amino)-17-((R)-5-methoxy-5-oxopentan-2-yl)-10,13-dimethyl-12-oxohexadecahydro-1H-cyclopenta[a]phenanthrene-3,7-diyl diacetate (Compound 5)

To a solution of amine (0.5 g, 1 mmol) in anhydrous CH$_2$Cl$_2$, N-methylmorpholine (0.12 ml, 1.1 mmol) was added and the mixture cooled to −20° C., after which ethylchloroformate (0.1 ml, 1 mmol) was added. The reaction temperature was maintained at −20° C. for 5 min, then it was allowed to stir at 0° C. for 2-3 hrs. Finally, the reaction mixture was treated with aq. HCl, aq. NaHCO$_3$ and aq. NaCl and then dried over anhydrous Na$_2$SO$_4$. The organic phase was concentrated in vacuo and the residue purified by column chromatography on silica gel by using ethyl acetate/hexane (2:1) to give the pure Compound 5. Yield (0.35 g, 70%); Mp 82-85° C. $^1$H NMR (200 MHz, CDCl$_3$, d): 0.78 (d, 3H, CH$_3$), 1.07 (s, 3H, CH$_3$), 1.23 (s, 3H, CH$_3$), 1.00-2.52 (m, 28H, steroidal —CH and CH2), 1.68 (s, 3H, CH$_3$CH$_2$O—), 2.02 (s, 3H, CH$_3$CO), 2.05 (s, 3H, CH$_3$CO), 3.67 (s, 3H, CH$_3$OCO), 4.06 (br d, 1H, 7-CH), 4.60 (m, 1H, 3-CH), 4.71 (q, 2H, —OCH$_2$), 4.95 (d, 1H, 11-CH), 5.29 (d, 1H NH amide).

Example 7

Synthesis of (3R,5S,7R,10S,11S,13R)-17-((R)-5-methoxy-5-oxopentan-2-yl)-10,13-dimethyl-12-oxo-11-(pyrrolidine-2-carboxamido)hexadecahydro-1H-cyclopenta[a]phenanthrene-3,7-diyl diacetate (Compound 6)

To a solution of N-boc protected proline derivative of diacetate methyl cholate (0.175 g 0.24 mmol) in anhydrous DCM, the solution was kept at 0° C. Trifluoroacetic acid (0.09 ml, 1.22 mmol) was added dropwise by a syringe. The reaction mixture was kept at 0° C. for 1-2 hrs. The reaction mixture was treated with chilled NaHCO$_3$ several times and extract with DCM, organic phase was separated and dried over anhydrous Na$_2$SO$_4$. The organic phases were concentrated in vacuo and the residue purified by column chromatography on silica gel using ethyl methanol/DCM (10%) to give the pure Compound 6 as thick yellow liquid. Yield (0.130 g, 86.6%); M.P. 102.6-103.8° C.; $^1$H NMR (200 MHz, CDCl$_3$, δ) −0.76 (d, 3H, CH$_3$), 1.09 (s, 3H, CH$_3$), 1.24 (s, 3H, CH$_3$), 1.00-2.52 (m, 28H, steroidal —CH and —CH2), and 3' and 4'-CH$_2$ of Proline), 2.03 (s, 3H, CH$_3$CO), 2.04 (s, 3H, CH$_3$CO), 2.84-3.10 (m, 2H, 5'-CH$_2$ of Proline), 3.66 (s, 3H, CH$_3$OCO), 3.77-3.83 (m, 1H, 2'-CH of Proline), 4.53-4.67 (m, 1H, 3-CH), 4.94 (d, 1H, C-11 —CH), 5.03 (m, 1H, 7-CH), 4.94 (d, 1H, 11-CH), 8.13 (d, 1H, C-11 amide —NH).

Example 8

Synthesis of (3R,5S,7R,10S,11S,13R)-11-(2-((tert-butoxycarbonyl)amino)-3-hydroxypropanamido)-17-((R)-5-methoxy-5-oxopentan-2-yl)-10,13-dimethyl-12-oxohexadecahydro-1H-cyclopenta[a]phenanthrene-3,7-diyl diacetate (Compound 7)

To a solution of N-Boc protected L-serine (0.25 g, 1.2 mmol) in anhydrous DMF, 1-Ethyl-3-(3-dimethylaminopropyl)-carbodiimide (EDC, 0.27 g, 1.4 mmol), hydroxybenzotriazole (0.06 g, 0.48 mmol) and DMAP (0.02 g, 0.2 mmol) was added and the mixture was cooled to 0° C. The reaction temperature was maintained at 0° C. for 5-10 mins, then a DMF solution of amine (0.5 g, 1 mmol) was added dropwise over 5 min at 0° C. Then the reaction mixture was stirred for 3 hrs at room temperature. Finally, the reaction mixture was treated with aq. HCl, aq, NaHCO$_3$, aq. NaCl and then dried over anhydrous Na$_2$SO$_4$. The organic phase was concentrated in vacuo and the residue purified by column chromatography on silica gel by using ethyl acetate/hexane (2:1) to give the pure Compound 7. Yield (0.580 g, 85%); $^1$H NMR (500 MHz, CDCl$_3$): −δ 6.69 (d, 1H), 5.42 (d, 1H), 4.96 (d, 1H), 5.04 (m, 1H), 4.58 (m, 1H), 4.04-4.20 (m, 2H), 3.66 (s, 3H), 3.62-3.70 (m, 1H), 2.02 (s, 3H), 2.05 (s, 3H), 1.46 (s, 9H), 1.23 (s, 3H), 1.08 (s, 3H), 0.76 (d, 3H).

Example 9

(3R,5S,7R,10S,11S,13R)-11-(1H-benzo[d][1,2,3]triazol-1-yl)-17-((R)-5-methoxy-5-oxopentan-2-yl)-10,13-dimethyl-12-oxohexadecahydro-1H-cyclopenta[a]phenanthrene-3,7-diyl diacetate (Compound 8)

To a solution of 2-(trimethylsilyl) phenyl trifluoromethanesulfonate (0.35 ml, 1.5 mmol) in anhydrous acetonitrile, Cesium fluoride (0.9 g, 2.4 mmol) was added. Finally C-11 azide (0.7 g, 1.2 mmol) in dry acetonitrile was added dropwise by syringe. The reaction mixture was kept at room temperature overnight. The reaction mixture was treated with chilled water and ethyl acetate, and organic phase was separated and dried over anhydrous Na$_2$SO$_4$. The organic phases were concentrated in vacuo and the residue purified by column chromatography on silica gel using ethyl acetate/hexane (2:1) to give the pure Compound 8 as cream colored solid. M.P. 106-109° C.; NMR (500 MHz, CDCl$_3$): δ 8.9 (d, 1H), 7.51 (s, 1H), 7.36-7.4 (m, 2H), 6.25 (d, 1H), 5.1 (s, 1H), 4.31 (m, 1H), 3.64 (s, 3H) 2.14 (s, 3H), 2.05 (s, 3H), 1.95 (s, 2H), 1.86 (s, 2H), 1.26 (s, 3H), 1.22 (s, 3H), 0.73 (d, 3H).

Example 10

Synthesis of (3R,5S,7R,10S,11S,13R)-11-(1-(tert-butoxycarbonyl)pyrrolidine-2-carboxamido)-17-((R)-5-methoxy-5-oxopentan-2-yl)-10,13-dimethyl-12-oxohexadecahydro-1H-cyclopenta[a]phenanthrene-3,7-diyldiacetate (Compound 9)

To a solution of N-Boc protected proline (0.26 g, 1.2 mmol) in anhydrous DMF, 1-Ethyl-3-(3-dimethylaminopropyl)-carbodiimide (EDC) (0.27 g, 1.4 mmol), hydroxylbenzotriazole (0.06 g, 0.5 mmol) and DMAP (0.02 g, 0.2 mmol) was added and the mixture was cooled to 0° C. The reaction temperature was maintained at 0° C. for 5-10 mins, then a DMF solution of amine (0.5 g, 1 mmol) was added drop wise over 5 min at 0° C. Then the reaction mixture was stirred for 3 hrs at room temperature. Finally, the reaction mixture was treated with aq. HCl, aq. NaHCO$_3$, aq. NaCl and then dried over anhydrous Na$_2$SO$_4$. The organic phase was concentrated in vacuo and the residue purified by column chromatography on silica gel by using ethyl acetate/hexane (2:1) to give the pure Compound 9. Yield (0.530 g, 77%); Mp. 114-118° C. $^1$H NMR (500 MHz, CDCl$_3$): 0.78 (d, 3H, CH$_3$), 1.07 (s, 3H, CH$_3$), 1.25 (s, 3H, CH$_3$), 1.00-2.52 (m, 28H, steroidal —CH and CH$_2$), and 3' and 4'-CH$_2$ of Boc-Pro), 1.51 (s, 9H, Boc-3CH$_3$), 2.01 (s, 3H, CH$_3$CO), 2.03 (s, 3H, CH$_3$CO), 3.31 (m, 2H, 5'-CH$_2$ of Boc-Pro), 3.66 (s, 3H, CH$_3$OCO). 4.36 (br d, 1H, 7-CH), 4.59 (m, 1H, 3-CH), 4.94 (d, 1H, 11-CH), 5.07 (t, 1H, 2'-CH of Boc-Pro).

Example 11

Synthesis of (3R,5S,7R,10S,11S,13R)-11-(isopropylamino)-17-((R)-5-methoxy-5-oxopentan-2-yl)-10,13-dimethyl-12-oxohexadecahydro-1H-cyclopenta[a]phenanthrene-3,7-diyl diacetate (Compound 10)

To a solution of amine (0.4 g, 0.75 mmol) in anhydrous DMF, anhydrous potassium carbonate (0.63 g, 4.6 mmol) was added. Finally isopropyliodide (0.15 ml, 1.5 mmol) was added with the help of syringe. The reaction mixture was then allowed to stir at 60-70° C. for 24 hrs. The reaction mixture was treated with chilled water and ethyl acetate, and organic phase was separated and dried over anhydrous Na$_2$SO$_4$. The organic phases were concentrated in vacuo and the residue purified by column chromatography on silica gel using ethyl acetate/hexane (2:1) to give the pure Compound 10 as thick yellow liquid. Yield (0.35 g, 81%); $^1$H NMR (200 MHz, CDCl$_3$, d): 0.77 (d, 3H, CH$_3$), 1.05 (s, 3H, CH$_3$), 1.16 (s, 3H, CH$_3$), 1.00-2.52 (m, 28H, steroidal —CH and CH$_2$), 1.59 (d, 6H), 2.00 (s, 3H, CH$_3$CO), 2.02 (s, 3H, CH$_3$CO), 2.99 (d, 1H, —CH of isopropyl), 3.58 (d, 1H, 11-CH), 3.67 (s, 3H, —OCH$_3$), 4.63 (m, 1H, 3-CH), 4.90 (d, 1H, 7-CH).

Example 12

Anti-Cancer Screening Results of Synthesized Compounds

Anti-cancer screening results of synthesized compounds (1 to 10) and their IC$_{50}$ and MIC values against human cancer cell lines are summarized in Table 1.

TABLE 1

Cell lines and IC$_{50}$, MIC (μg/mL)

| Sr. No. | Compound ID | THP-1 (Human acute monocytic leukemia cell line) | | HeLa (Human Cervix epithelioid carcinoma cell line) | | Panc-1 (Human pancreas carcinoma cell line) | | A549 (Human lung adenocarcinoma epithelial cell line) | |
|---|---|---|---|---|---|---|---|---|---|
| | | IC 50 | MIC | IC 50 | MIC | IC 50 | MIC | IC 50 | MIC |
| 1 | 1 | >100 | >100 | 7.02 | 99.07 | >100 | >100 | >100 | >100 |
| 2 | 2 | >100 | >100 | 6.59 | >100 | >100 | >100 | >100 | >100 |
| 3 | 3 | >100 | >100 | 9.76 | >100 | >100 | >100 | >100 | >100 |
| 4 | 4 | >100 | >100 | 15.23 | 85.94 | >100 | >100 | >100 | >100 |
| 5 | 5 | >100 | >100 | 34.24 | >100 | >100 | >100 | >100 | >100 |
| 6 | 6 | >100 | >100 | >100 | >100 | >100 | >100 | >100 | >100 |
| 7 | 7 | 76.18 | >100 | 18.2 | >100 | >100 | >100 | >100 | >100 |
| 8 | 8 | 29.9 | >100 | 20.34 | >100 | 50.02 | >100 | 20.04 | >100 |
| 9 | 9 | 45.95 | >100 | 18.55 | >100 | 15 | >100 | 52 | >100 |
| 10 | 10 | >100 | >100 | 11.57 | >100 | >100 | >100 | >100 | >100 |
| | Paclitaxel | 0.1374 | 5.8140 | 0.0048 | 0.075 | 0.1279 | 5.7150 | 0.0035 | 0.0706 |

IC$_{50}$: The concentration of sample required to inhibit 50% of the cell proliferation,
MIC: The concentration of sample required to inhibit 90% of the cell proliferation

Example 13

Anti TB IC 50 and MIC Chart In Vitro and Ex-Vivo Data

Table 2 shows Anti TB screening results of synthesized compounds (2, 7 to 9) and their IC$_{50}$ and MIC values against *M. Tuberculosis*.

TABLE 2

| Sr. No. | Compound ID | In Vitro against M. Tuberculosis H37Ra (DORMANT) | | In Vitro against M. Tuberculosis H37Ra (ACTIVE) | | Ex Vivo: Infection Model (DORMANT) | | Ex Vivo: Infection Model (ACTIVE) | |
|---|---|---|---|---|---|---|---|---|---|
| | | IC 50 | MIC | IC 50 | MIC | IC 50 | MIC | IC 50 | MIC |
| | | | | | ug/mL | | | | |
| 1 | 2 | 0.17 | 2.43 | 0.64 | 2.63 | 0.13 | 1.55 | 0.25 | 2.8 |
| 2 | 7 | 0.58 | 8.6 | 1.24 | 9.03 | 1.32 | 23.84 | 1.96 | 27.3 |
| 3 | 8 | 1.27 | 7.15 | 1.08 | 9.79 | 1.65 | 8.16 | 1.11 | 8.6 |
| 4 | 9 | 2.024 | 8.91 | 0.92 | 9.41 | 3.42 | 26.3 | 4.16 | 26.78 |
| 5 | RIFAMPICIN | 0.0014 | 0.043 | 0.0018 | 0.048 | 0.0018 | 0.048 | 0.0021 | 0.051 |
| 6 | ISONIAZID | .0023 | 0.075 | 0.0019 | 0.074 | 0.0024 | 0.0078 | 0.0024 | 0.075 |

Advantages of the invention:
a. Bile acid derivatives with C-11 functionality shows anticancer activity.
b. Bile acid derivatives with C-11 functionality shows antituberculosis activity.
c. Azido groups are versatile and could be conveniently transformed into 1,2,3-triazole via click reaction and reduced to amines which in turn could be alkylated or acylated to provide large number of biologically active new molecules.
d. Coupling of C-11 amine with chiral amino acids may provide chiral catalysts for various reactions.

We claim:
1. A compound or a pharmaceutically acceptable salt thereof selected from the group consisting of

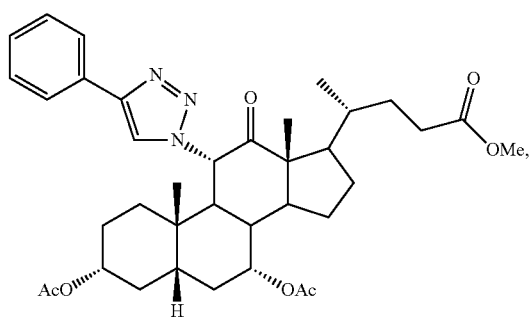

1

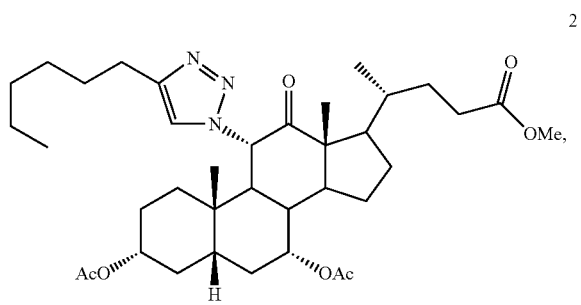

2

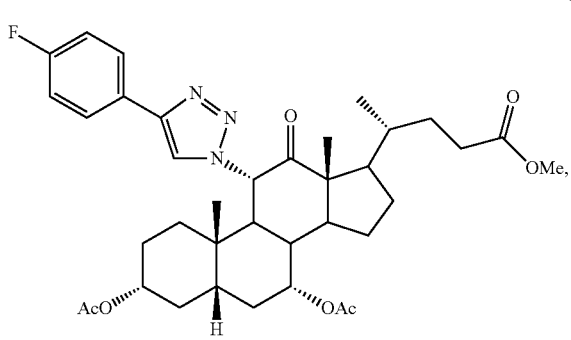

3

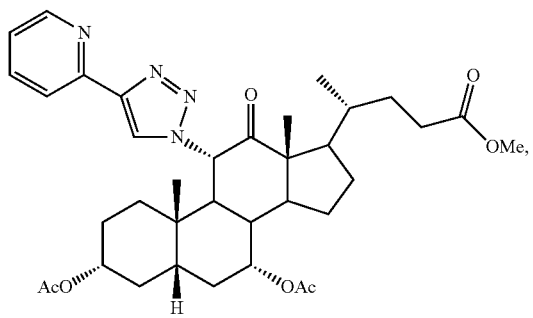

4

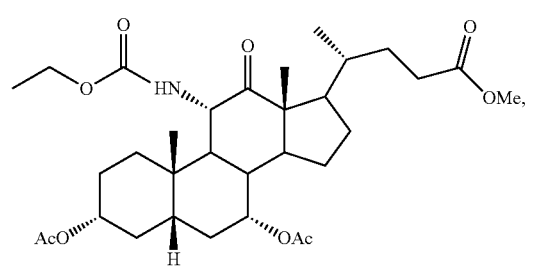

5

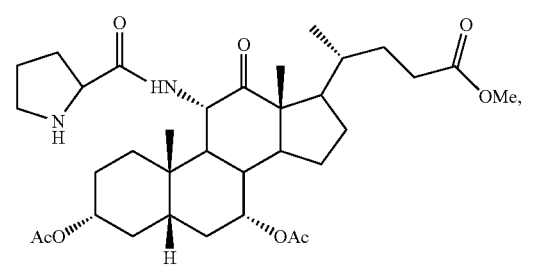

6

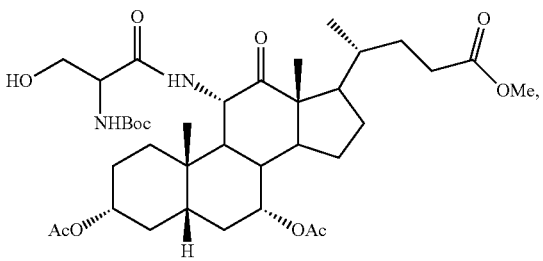

7

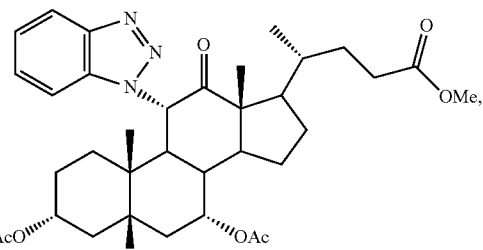

8

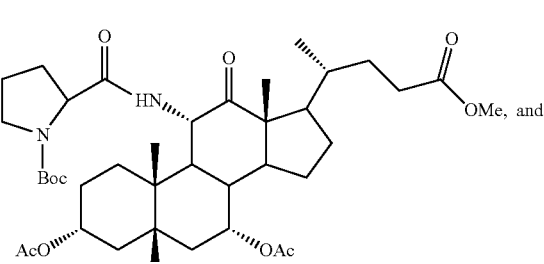

9

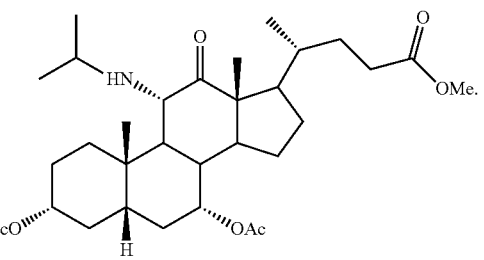

10

2. A pharmaceutical composition comprising an effective amount of a compound of Formula (I) according to claim 1.

3. The process for preparation of a compound of Formula (I) according to claim 1, comprising the steps of:
   a) esterifying cholic acid using methanol in the presence of an acid catalyst and purifying product of reaction to obtain methyl cholate;
   b) protecting the hydroxyl groups at C-3 and C-7 of methyl cholate of step (a) as acetates or benzoates by using acetic anhydride or benzoyl chloride to obtain 3,7-diacetoxy or dibenzoyloxy methyl cholate;
   c) oxidizing the hydroxyl group at C-12 of methyl cholate of step (b) to obtain 3,7-diacetoxy or dibenzoyloxy-12-oxo methyl cholate;
   d) brominating 3,7-diacetoxy or dibenzoyloxy-12-oxo methyl cholate of step (c) using bromine in benzene to obtain 3,7-diacetoxy or dibenzoyloxy-11-bromo-12-oxo methyl cholate;
   e) substituting the bromo group in 3,7-diacetoxy or dibenzoyloxy-11-bromo-12-oxo methyl cholate of step (d)

using sodium azide in DMF solvent to obtain 3,7-diacetoxy or dibenzoyloxy-11-azido-12-oxo methyl cholate; and f) alkylating, acylating or coupling of different amino acids, alkynyl compounds with compound of step (e) or reduction compound of step (e) to give compound of Formula (I);

wherein, the process optionally comprises reduction of azido group in 3,7-diacetoxy or dibenzoyloxy-11-azido-12-oxo methyl cholate of step (e) using triphenyl phosphine followed by reaction with water to obtain 3,7-diacetoxy or dibenzoxy-11-amino-12-oxo methyl cholate.

4. The process according to claim 3, wherein alkylation in step (f) is carried out using different short and long chain alkyl halides with or without additional amino functionality, comprising the steps of:
  a) adding anhydrous potassium carbonate to a solution of 3,7-diacetoxy or dibenzoyloxy-11-amino-12-oxo methyl cholate in anhydrous DMF to obtain a mixture;
  b) adding alkyl halide to the mixture of step (a) to obtain a reaction mixture; and
  c) stirring the reaction mixture of step (b) followed by work-up afforded the desired pure product.

5. The process according to claim 3, wherein acylation in step (f) is carried out using different short and long chain alkyl chloroformates comprising the steps of:
  a) adding N-methylmorpholine to a solution of 3,7-diacetoxy or dibenzoyloxy-11-amino-12-oxo methyl cholate in anhydrous $CH_2Cl_2$ and cooling followed by addition of alkyl chloroformate to obtain a reaction mixture; and
  b) stirring the reaction mixture of step (a) followed by work-up afforded the desired pure product.

6. The process according to claim 3, wherein coupling reaction of different amino acids in step (f) comprises the steps of:
  a) adding 1-Ethyl-3-(3-dimethylaminopropyl) carbodiimide (EDC), hydroxylbenzo-triazoleanddimethylaminopyridine (DMAP) to a solution of N-Boc protected amino acid in anhydrous DMF and cooling to obtain a mixture;
  b) adding dimethylformamide (DMF) solution of 3,7-diacetoxy or dibenzoyloxy-11-amino-12-oxo methyl cholate to the mixture of step (a) to obtain a reaction mixture; and
  c) stirring the reaction mixture of step (b) followed by work-up afforded the desired pure product.

7. The process according to claim 3, wherein coupling reaction of different alkynyl compounds in step (f) comprises the steps of:
  a) dissolving 3,7-diacetoxy or dibenzoyloxy-11-azido-12-oxo methyl cholate and an alkyne selected from 1-octyne, phenyl acetylene, 4-fluorophenyl acetylene, and 2-ethynyl pyridine in $DMF/H_2O$ followed by addition of $CuSO_4.5H_2O$ and sodium ascorbate to obtain a reaction mixture; and
  b) irradiating the reaction mixture in microwave followed by work-up afforded the desired pure product.

8. The process according to claim 3, wherein salts of C-11 functionalized bile acid derivatives of Formula (I) compounds are prepared by hydrolysis of the ester functionality at C-24 position with alkali or alkaline earth metal hydroxide.

9. A method of treating cancer by administering to the host an effective amount of a pharmaceutical composition comprising a compound according to Formula (I):

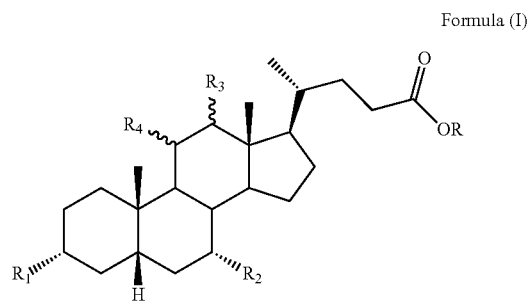

Formula (I)

wherein, R is selected from hydrogen, linear or branched alkyl group;

$R_1$ and $R_2$ are selected from OH, OAc and OBz;

$R_3$ is selected from OH, =O; and $R_4$ is selected from long or short alkyl chain substituted amino group with or without additional amino group, heterocyclic group, amide group;

or a pharmaceutically acceptable salt thereof.

10. The method according to claim 9, wherein the host is a human.

11. The method according to claim 9, wherein the cancer is human cervix epithelioid carcinoma cell line cancer.

12. The method according to claim 9, wherein the compound of Formula (I) is selected from the group consisting of:

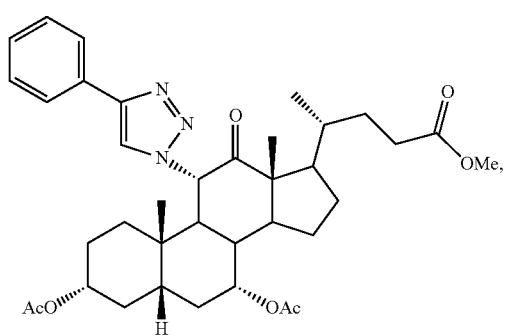

1

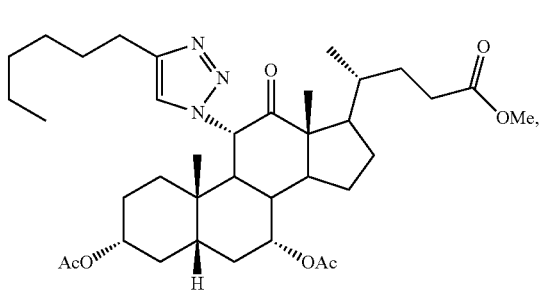

2

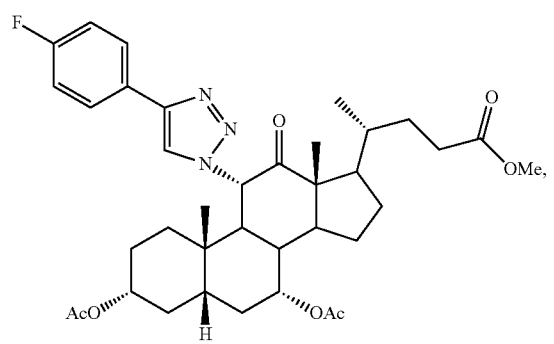
3
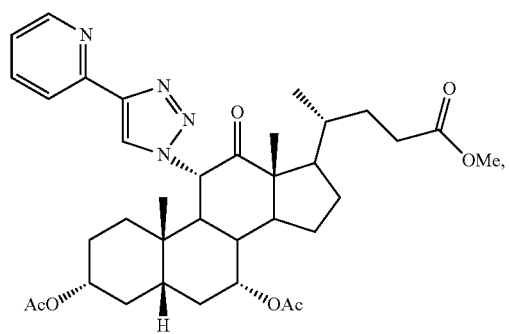
4
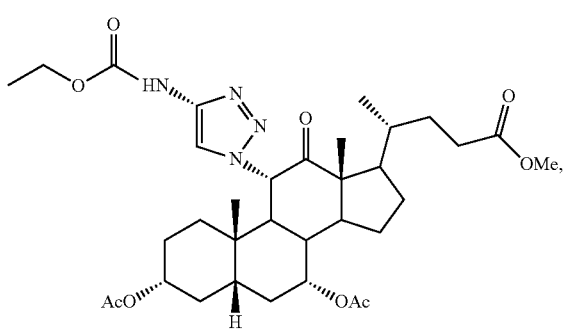
5
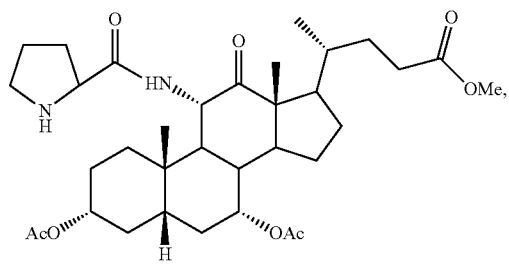
6
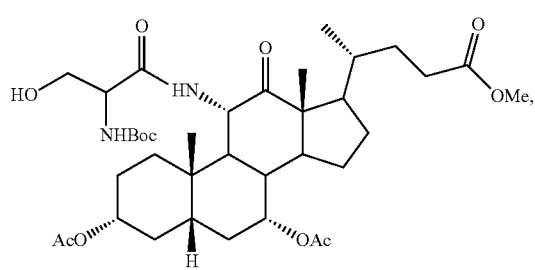
7
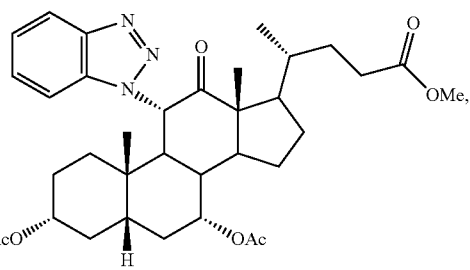
8
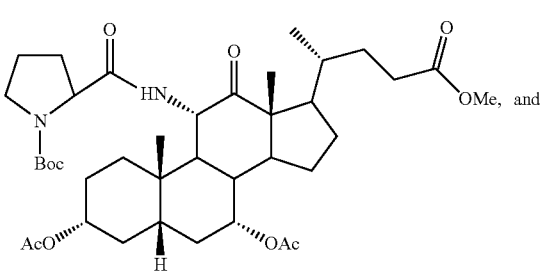
9
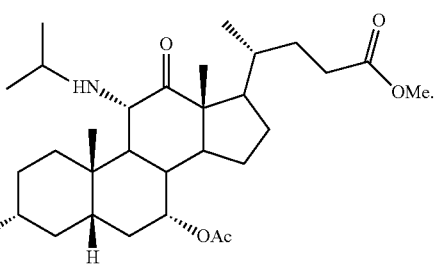
10
13. A method of treating mycobacterial infection of a host by administering to the host an effective amount of an antimycobacterial composition comprising a compound selected from:
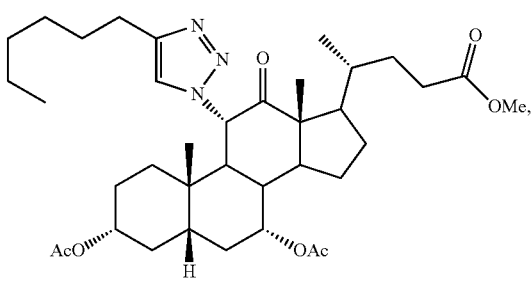
2
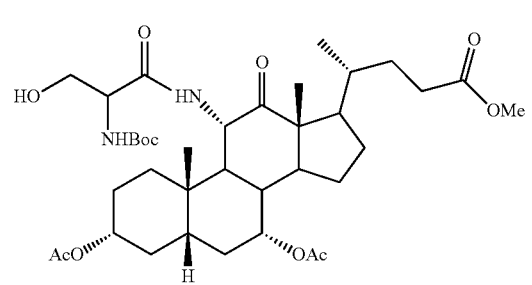
7

-continued
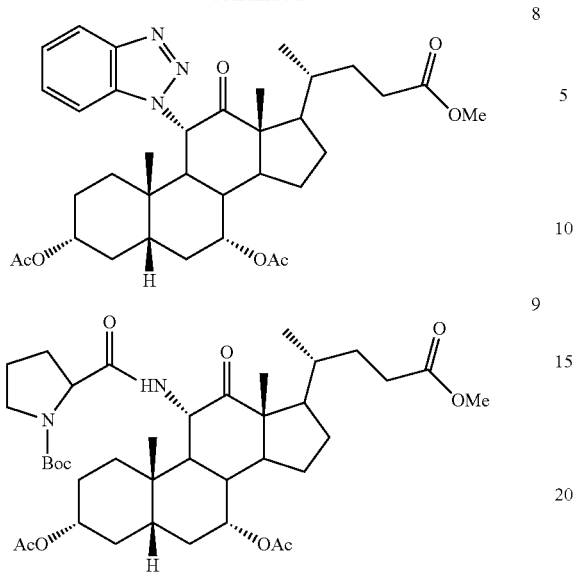
or a pharmaceutically acceptable salt thereof.
14. The method according to claim 13, in which the host is a human.
15. The method according to claim 13, wherein the mycobacterial infection is caused by mycobacterial species selected from *Mycobacterium tuberculosis* H37Ra or *Mycobacterium Bovis* BCG.
* * * * *